(12) United States Patent
Ruane et al.

(10) Patent No.: US 8,092,819 B2
(45) Date of Patent: Jan. 10, 2012

(54) IMPLANTABLE MEDICAL DEVICE COATED WITH A BIOACTIVE AGENT

(75) Inventors: Patrick H. Ruane, Redwood City, CA (US); Jeff P. Little, Lafayette, IN (US); Andrew P. Isch, Lafayette, IN (US)

(73) Assignee: Cook Medical Technologies LLC., Bloomington, IN (US)

( * ) Notice: Subject to any disclaimer, the term of this patent is extended or adjusted under 35 U.S.C. 154(b) by 544 days.

(21) Appl. No.: 11/655,300

(22) Filed: Jan. 19, 2007

(65) Prior Publication Data

US 2007/0207184 A1 Sep. 6, 2007

Related U.S. Application Data

(60) Provisional application No. 60/762,924, filed on Jan. 27, 2006.

(51) Int. Cl.
- *A61F 13/00* (2006.01)
- *A61F 2/06* (2006.01)
- *C07H 21/04* (2006.01)

(52) U.S. Cl. ...... 424/422; 623/1.44; 623/1.42; 536/24.5

(58) Field of Classification Search ............... None
See application file for complete search history.

(56) References Cited

U.S. PATENT DOCUMENTS

| | | |
|---|---|---|
| 2,467,926 A | 4/1949 | Ardis |
| 2,721,858 A | 10/1955 | Joyner et al. |
| 2,784,127 A | 3/1957 | Joyner et al. |
| 4,444,933 A | 4/1984 | Columbus et al. |
| 4,739,762 A | 4/1988 | Palmaz |
| 5,133,732 A | 7/1992 | Wiktor |
| 5,292,331 A | 3/1994 | Boneau |
| 5,421,955 A | 6/1995 | Lau et al. |
| 6,090,127 A | 7/2000 | Globerman |
| 6,153,252 A | 11/2000 | Hossainy et al. |
| 6,770,729 B2 | 8/2004 | Van Antwerp |
| 7,094,765 B1 | 8/2006 | Iveraen et al. |
| 2004/0034409 A1 | 2/2004 | Heublein et al. |
| 2004/0193255 A1* | 9/2004 | Shanley et al. ............ 623/1.42 |
| 2004/0215313 A1* | 10/2004 | Cheng ...................... 623/1.11 |
| 2004/0243225 A1 | 12/2004 | Ragheb et al. |
| 2006/0002973 A1 | 1/2006 | Barry et al. |

FOREIGN PATENT DOCUMENTS

| | | |
|---|---|---|
| WO | WO 00/40278 | 7/2000 |
| WO | WO 00/41647 | 7/2000 |
| WO | WO 00/44287 | 8/2000 |
| WO | WO 03/006180 | 1/2003 |

OTHER PUBLICATIONS

International Search Report for PCT/US2007/002183.

Leonard et al., "Synthesis and degradation of poly (alkyl α-cyanoacrylates)" J. Appl. Polym. Sci, 10, pp. 259-272 (1966).

Vauthier, C. et al. "Poly(alkylcyanoacrylates) as biodegradable materials for biomedical applications" Advanced Drug Delivery Reviews 55, pp. 519-548 (2003).

Zimmer, A., "Antisense Oligonucleotides Delivery with Polyhexylcyanoacrylate Nanoparticles as Carriers", Methods: A Companion to Methods in Enzymology 18, pp. 288-295 (1999).

Fontana, G. et al., "Amoxicillin-loaded polyethylcyanoacrylate nanoparticles: Influence of PEG coating on the particle size, drug release rate and phagocytic uptake" Biomaterials 22, pp. 2857-2865 (2001).

Li, S. et al., "In vitro release of protein from poly(butylcyanoacrylate) nanocapsules with an aqueous core" Colloid Poly Sci 283, pp. 480-485 (2005).

Wang, Y., et al. "A tough biodegradable elastomer" Nature Biotechnology 20, pp. 602-606 (2002).

Schwab, G. et al. "Antisense oligonucleotides adsorbed to polyalkylcyanoacrylate nanoparticles specifically inhibit mutated Ha-ras-mediated cell proliferation and tumorigenicity in nude mice" Proc Natl Acad Sci U S A. 91(22):10460-4 (1994).

Couvreur, P. et al. "Tissue distribution of antitumor drugs associated with polyalkylcyanoacrylate nanoparticles" J Pharm Sci. 69 2 :199-202 1980.

Park, D. H. et al. "In vitro Degradation and Cytotoxicity of Alkyl 2-Cyanocrylate Polymers for Application to Tissue Adhesives" J. Appl. Polym. Sci 89, pp. 3272-3278 (2003).

Lambert, Gregory, "Polyalkylcyanoacrylate Nanospheres and Nanocapsules for the Delivery of Antisense Oligonucleotides" Journal of Dispersion Science and Technology, vol. 24, Nos. 3&4, pp. 439-452 (2003).

Lambert, G. et al., "Nanoparticulate Systems for the Delivery of Antisense oligonucleotides" Advanced Drug Delivery Reviews, 47, pp. 99-112 (2001).

Weyermann, J. et al., "Comparison of Antisense Oligonucleotide Drug Delivery systems" Journal of Controlled Release, 100, pp. 411-423 (2004).

Chavany, C. et al., "Polyalkylcyanoacrylate Nanoparticles as Polymeric Carriers for Antisense Oligonucleotides", Pharmaceutical Research, vol. 9, No. 4, pp. 441-449 (1992).

Domb, A. J and Wiseman, D. M. eds. "Handbook of Biodegradable Polymers 10: Poly(Alkylcyanoacrylates)" pp. 183-202, 1997.

* cited by examiner

*Primary Examiner* — Tracy Vivlemore
(74) *Attorney, Agent, or Firm* — Brinks Hofer Gilson & Lione

(57) ABSTRACT

The present invention provides an implantable medical device comprising a bioactive agent and poly(alkyl cyanoacrylate) polymer. In one embodiment of the invention, the bioactive agent is a water-soluble material, such as an antisense agent.

20 Claims, 3 Drawing Sheets

IMPLANTABLE MEDICAL DEVICE COATED WITH A BIOACTIVE AGENT

RELATED APPLICATIONS

This non-provisional patent application claims priority to U.S. Provisional Patent Application No. 60/762,924, filed Jan. 27, 2006, the contents of which are incorporated by reference in their entirety.

FIELD OF THE INVENTION

This invention relates generally to human and veterinary medical devices and more particularly to medical devices incorporating drugs or bioactive agents.

BACKGROUND OF THE INVENTION

It has become common to treat a variety of medical conditions by introducing an implantable medical device partly or completely into the esophagus, trachea, colon, biliary tract, urinary tract, vascular system or other location within a human or veterinary patient. For example, many treatments of the vascular system entail the introduction of a device such as a stent, a catheter, a balloon, a wire guide, a cannula, or the like.

For certain applications, the medical device is coated with a bioactive agent adapted to expose tissue within the body to the bioactive agent over a desired time interval, such as by releasing the bioactive agent. Desirably, the bioactive agent is released within the body at a reproducible and predictable fashion so as to optimize the benefit of the bioactive agent to the patient over the desired period of time.

Providing coated medical devices adapted to release a bioactive agent at a desired rate over a period of time is one challenge in designing implantable medical devices. For example, a coated medical device may release a bioactive agent at a greater rate than desired upon implantation, and subsequently release the bioactive agent at a slower rate than desired at some time after implantation. What is needed is a medical device that provides for release of one or more bioactive agents over a period of time that is desired for one or more bioactive applications, desirably at an optimal elution rate from the device.

Various approaches can be used to control the release of bioactive agents from an implantable medical device. The design configuration of an implantable device can be adapted to influence the release of a bioactive agent from the device. For example, a bioactive agent can be included in the implantable medical device according to various configurations. In some devices, the bioactive agent is contained within an implantable frame or coating on the surface of the implantable frame. An implantable frame may comprise a bioabsorbable material within or coated on the surface of the implantable frame, and the bioabsorbable material can optionally be mixed with a bioactive agent. Some implantable medical devices comprise an implantable frame with a porous biostable material optionally mixed with or coated on top of a bioactive agent. Implantable medical devices can also comprise a biostable material containing a removable material and a bioactive agent, where removal of the removable material forms pores that allow release of the bioactive agent.

The release of the bioactive agent may also be influenced by several factors, such as the molecular size of the polymer, the concentration of the agent in the polymer matrix, the glass transition point (Tg) of the polymer matrix, the crystallinity and solubility of the bioactive agent in various environments, the morphology of the coating and the thickness of the coating. A common release profile shows an initial release of a large amount of the agent (burst release), followed by a slow and gradual release leading to a plateauing effect.

There is a need for a medical device capable of releasing a bioactive agent over a desired time period, preferably as needed in the local area surrounding the site of medical intervention to promote a therapeutically desirable outcome. For example, it may be desirable for a medical device to provide a first rate of elution of the bioactive agent from an implanted medical device over an initial period of time and then a second rate of elution of the bioactive agent during a subsequent period of time. There is also a need for such a medical device capable of withstanding the flexion and impact that accompany the transportation and implantation of the device, for example by providing a high durability device coating adapted to deliver a bioactive agent within a body vessel.

An illustrative example involving the use of an implantable medical device is in the treatment of vascular disease. Bioactive agents can be applied to an implantable stent or valve to treat or mitigate undesirable vascular conditions such as restenosis or thrombosis formation. Procedures for mitigating such conditions may include implantation of a device comprising a bioactive agent.

For example, the implantation of stents during angioplasty procedures has substantially advanced the treatment of occluded body vessels. Angioplasty procedures may be employed to widen a narrowing or occlusion of a blood vessel by dilation with a balloon. Occasionally, angioplasty may be followed by an abrupt closure of the vessel or by a more gradual closure of the vessel, commonly known as "restenosis." Acute closure may result from an elastic rebound of the vessel wall and/or by the deposition of blood platelets and fibrin along a damaged length of the newly opened blood vessel. In addition, restenosis may result from the natural healing reaction to the injury to the vessel wall (known as intimal hyperplasia), which involves the migration and proliferation of medial smooth muscle cells that continues until the vessel is again occluded. To prevent such vessel occlusion, stents have been implanted within a body vessel. However, restenosis may still occur over the length of the stent and/or past the ends of the stent where the inward forces of the stenosis are unopposed.

To reduce this problem, one or more bioactive agents may be administered to the patient. For example, a bioactive agent may be locally administered through a catheter positioned within the body vessel near the stent, or by coating the stent with the bioactive agent. One such bioactive is the antisense drug RESTEN-NG™ (NEUGENE® AVI Biopharma, Portland, Oreg.), which has applications in the treatment of restenosis in balloon injured coronary arteries. However, the delivery of water-soluble drugs, such as antisense drugs, presents particular problems. Such drugs are quickly eluted when subjected to an aqueous environment present within the body. As a result, such drugs can be eluted from a medical device prior to placement of the device or before an effective dose can be delivered at the target site.

Durable polymer drug carriers have been investigated for delivering water-soluble drugs. However, such polymers have the disadvantage of causing thrombosis and/or an inflammatory response over time. Although biodegradable polymers have been regarded as being more suitable drug carriers on medical devices, such as stents, those polymers currently used have not been effective for controlling the release of water-soluble drugs.

SUMMARY

On aspect of the present invention provides an implantable medical device having a bioactive agent and a poly(alkyl cyanoacrylate) polymer (PACA) present on at least one surface. In addition to the PACA, at least one other biodegradable polymer may also be present. In one embodiment, the bioactive agent is water-soluble. In another embodiment, the solubility of the bioactive agent in water is greater than 2.5 g/L.

In one embodiment, the bioactive agent is coated on the least one surface of the medical device, the poly(alkyl cyanoacrylate) polymer is coated on at least a portion of the bioactive agent and the biodegradable polymer is coated on at least a portion of the poly(alkyl cyanoacrylate) polymer.

In another embodiment, a mixture of the bioactive agent and the poly(alkyl cyanoacrylate) polymer is coated on at least one surface. In yet another embodiment, a biodegradable polymer is coated on at least a portion of the mixture of the bioactive agent and the poly(alkyl cyanoacrylate) polymer.

In certain embodiments, the poly(alkyl cyanoacrylate) polymer and the biodegradable polymer are present at a weight ratio of between 400:1 and 1:400.

In certain embodiments, the release of the bioactive agent into an environment in which the implantable medical device is placed is modulated by the poly(alkyl cyanoacrylate) polymer. The poly(alkyl cyanoacrylate) polymer contains an alkyl group consisting of between 1 and 12 carbon atoms. In various embodiments, the poly(alkyl cyanoacrylate) polymer is poly(n-butyl cyanoacrylate), poly(isohexyl cyanoacrylate), poly(n-hexyl cyanoacrylate) and poly(n-octyl cyanoacrylate).

In certain embodiments, the biodegradable polymer is selected from a group consisting of PLA (polylactic acid), PLLA, PDLA, PLGA, PEG, PGA and block copolymers of these compounds.

In certain embodiments, the bioactive agent is an anti-thrombocytic, anti-inflammatory, an anti-proliferative agent, an immunosuppressive, rapamycin, heparin or an antisense compound. The antisense compound can be a compound that inhibits cellular proliferation and/or restenosis. In one embodiment, the implantable medical device includes a vascular stent.

Another aspect of the present invention provides a method of manufacturing an implantable medical device by coating at least one surface of the device with a water-soluble bioactive agent and coating an alkyl cyanoacrylate monomer onto at least a portion of the water-soluble bioactive agent.

Yet another aspect of the present invention provides a method of delivering a water-soluble bioactive agent to a subject. The method includes inserting an implantable medical device into the subject's body. A layer including the water-soluble bioactive agent is present on a surface of the implantable medical device. At least a portion of this layer is overcoated by a layer including a poly(alkyl cyanoacrylate) polymer. The medical device is inverted for a time sufficient to allow at least a portion of the water-soluble bioactive agent to be released from the medical device.

DESCRIPTION OF THE ILLUSTRATIVE EMBODIMENTS

Definitions

Figure 1:
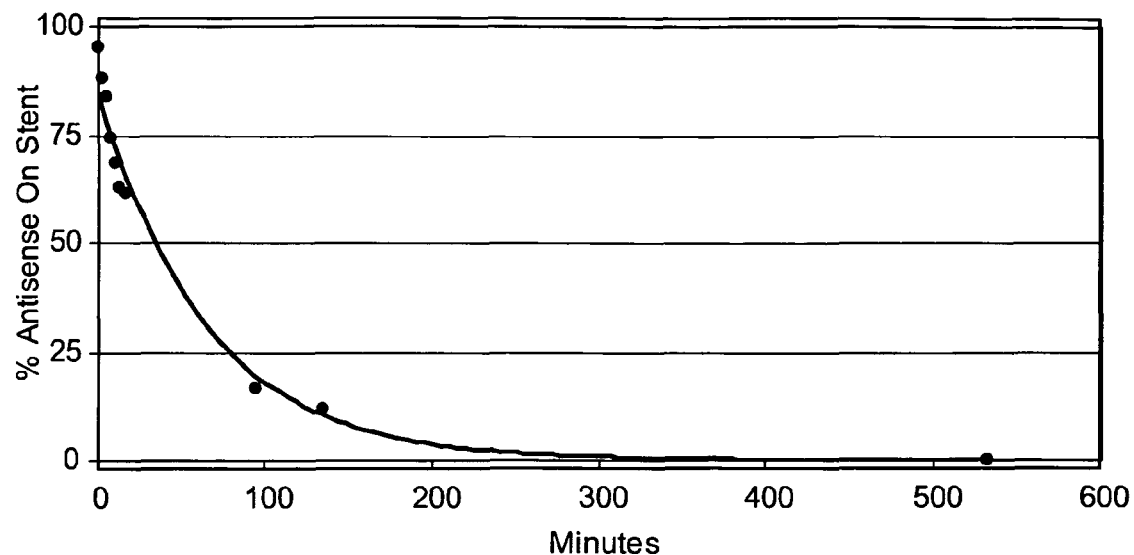
FIG. 1 is a graph showing the elution of the antisense drug from a 8×20 mm stent ultrasonically coated with a mixture of RESTEN-NG™ antisense drug and poly(n-butyl cyanoacrylate) and ultrasonically coated with an overcoat of polylactic acid. The elution followed first order kinetics with a $t_{1/2}$ of 44.7 minutes.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The terms "about" or "substantially" used with reference to a quantity includes variations in the recited quantity that are equivalent to the quantity recited, such as an amount that is insubstantially different from a recited quantity for an intended purpose or function.

The term "implantable" refers to an ability of a medical device to be positioned, partially or wholly, at a location within a body, such as within a body vessel. Furthermore, the terms "implantation" and "implanted" refer to the positioning of a medical device at a location, partially or wholly, within a body, such as within a body vessel.

The term "alloy" refers to a substance composed of two or more metals or of a metal and a nonmetal intimately united, such as by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

The terms "antisense" and "antisense oligonucleotide" refer to strands of natural or modified deoxyribonucleic acid (DNA) or ribonucleic acid (RNA) that inhibit the translation of the messenger ribonucleic acid (mRNA) to protein. These agents may inhibit the up-regulation of genes in the body (that is, they may inhibit the production of proteins in the body). The antisense therapeutics may inhibit or prevent the production of specific proteins that are up-regulated or activated in the disease process. Antisense therapeutics may bind to a specific mRNA as part of their mechanism of action. For the purposes of the invention, "antisense compounds" include both natural nucleic acid oligonucleotides and compounds having a modified backbone.

The term "biodegradable" refers to materials selected to dissipate upon implantation within a body, independent of which mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable", depending upon the mechanism by which the material dissipates. The prefix "bio" indicates that the erosion occurs under physiological conditions, as opposed to other erosion processes, caused for example, by high temperature, strong acids or bases, UV light or weather conditions.

A "biocompatible" material is a material that is compatible with living tissue or a living system by not being toxic or injurious and not causing immunological rejection.

A "non-bioabsorbable" or "biostable" material refers to a material, such as a polymer or copolymer, which remains in the body without substantial bioabsorption.

The phrase "controlled release" refers to the release of a material from a medical device at a predetermined rate. The predetermined rate may be determined by, for example, the presence of a carrier material or a barrier layer. In general, the rate of controlled release will be such that the material is released over a longer period that would be the case if the carrier material and/or barrier layer were not present. A controlled release may be constant or vary with time.

A controlled release may be characterized by a drug elution profile, which shows the measured rate that the material is removed from a material-coated device in a given solvent environment as a function of time. For example, a controlled release elution profile may include an initial burst release associated with the deployment of the medical device, followed by a more gradual subsequent release. A controlled release may be a gradient release in which the concentration of the material released varies over time or a steady state release in which the material is released in equal amounts over a certain period of time (with or without an initial burst release).

As used herein, the phrase "bioactive agent" refers to any pharmaceutically active agent that produces an intended therapeutic effect on the body to treat or prevent conditions or diseases. Bioactive agents include any suitable biologically-active chemical compounds, biologically derived components such as cells, peptides, antibodies, and polynucleotides, and radiochemical therapeutic agents, such as radioisotopes.

As used herein, a "mixture" refers to a combination of two or more substances in which each substance retains its own chemical identity and properties.

As used herein, a "barrier layer" is any layer that is placed over at least a portion of a bioactive agent present in or on an implantable medical device. The barrier layer may control the release of the bioactive agent from the device.

As used herein, a "carrier material" refers to a material that forms a mixture with bioactive agent on or in an implantable medical device. The carrier material may control the release of the bioactive agent from the medical device.

Medical Devices Containing Bioactive Agents

One aspect of the present invention provides an implantable medical device ("medical device") allowing for the release of a bioactive agent into the adjacent or surrounding tissue. One or more bioactive agents are provided for release from the medical device. The bioactive agents may be included, for example, as part of the base material forming the medical device itself, within a carrier material deposited on the medical device, as a separate layer deposited on the medical device that may be over coated with a barrier layer, or any combination of these. In certain embodiments, the release of the bioactive agent from the medical device depends, in part, upon the composition and configuration of the carrier material and/or the barrier layer.

Certain embodiments of the present invention provide medical devices including a carrier material and/or a barrier layer including a poly(alkyl cyanoacrylate) (PACA), a biodegradable polymer. The presence of PACA can provide for a controlled release of a bioactive agent from the implanted medical device. In certain embodiments, the release of the bioactive agent is delayed as compared with the release observed in the absence of PACA.

By allowing for the delayed release of the bioactive agent when the medical device is implanted, the medical devices of the present invention allow for amounts of the bioactive agent to be released for longer periods of time as compared to the release from previous devices. In various embodiments of the invention, less than 90 percent of the bioactive agent present on or in the medical device is released into an aqueous environment over a period of at least about 6 months, two months, one month, one week, one day, 6 hours, 4 hours, 2 hours, 1 hr, 30 minutes or 15 minutes.

Poly(Alkyl Cyanoacrylate) Polymers

In one embodiment of the present invention, PACA polymers offer particular advantages by allowing for the delayed release of a bioactive agent that is water soluble and therefore subject to rapid release from the medical device when exposed to an aqueous environment.

Suitable PACA polymers for use in the present invention include, for example, those prepared from alkyl cyanoacrylate monomers having an alkyl group containing 3 to 12 carbon atoms. For example, suitable PACA polymers include poly(n-butyl cyanoacrylate), poly(n-hexyl cyanoacrylate), poly(isohexyl cyanoacrylate) and poly(n-octyl cyanoacrylate).

Alkyl Cyanoacrylate Monomers

PACA polymers may be prepared by the polymerization of alkyl cyanoacrylate monomers. Preparation of alkyl cyanoacrylate monomers is described, for example, in U.S. Pat. No. 2,467,926 "Preparation of Monometic Alkyl α-Cyano-acrylates" filed Mar. 1, 1947, and in U.S. Pat. No. 2,721,858 "Method of Making α-Cyano-acrylates", filed Mar. 10, 1954, the contents of both of which are incorporated by reference.

Alkyl cyanoacrylate monomers used for the preparation of PACA polymers useful in the present invention include those compounds represented by:

$$H_2C=C(CN)-COOR,$$

where R is selected from $C_{1-12}$ alkyl groups, including cyclic and branched isomers. Alkyl cyanoacrylate monomers having various alkyl chain lengths can be synthesized by the methods of Leonard et al., "Synthesis and degradation of poly (alkyl α-cyanoacrylates)" J. Appl. Polym. Sci, 10, pp 259-72 (1966) and Fattal, E. et al., "Poly (alkylcyanoacrylates)" in Handbook of Biodegradable Polymers, Ed. Domb, A. J. et al., Hardwood Academic Publishers (1997). Alkylcyanoacrylate monomers also can be prepared from an appropriate alkylcyanoacetate. Alkylcyanoacetates, including ethyl-, butyl-, pentyl-, hexyl-, octyl- and decyl cyanoacetates are available from Sigma-Aldrich Corp., St Louis, Mo.

For example, butyl cyanoacrylate could be prepared as follows: paraformaldehyde (135 gm), 300 ml of methanol, 100 ml of diglyme (dimethyl ether of ethylene glycol), 2.0 ml of piperidine could be placed in a flask fitted with a mechanical stirrer and water cooled condenser. This mixture is heated until the methanol is refluxed vigorously. A 5-mole portion of butyl cyanoacetate (705 gm) (Sigma-Aldrich Corp., St Louis, Mo.) is added at a rate sufficient to maintain the reflux after removal of the external heat source. Methanol is distilled off until the vapor temperature reaches 88° C. Benzene (250 ml) is added, and water removed from the reaction mixture by azeotropic distillation. 3.5 mole of water is then removed by conventional distillation. 15 gm of phosphorus pentoxide is added, benzene removed under water aspiration, and residual benzene and diglyme removed at 3 mm Hg. Vacuum distillation is continued until the temperature reaches 160° C. to remove any residual butylcyanoacetate. At this point a receiver with small amounts of pyrogallol and phosphorus pentoxide is attached to the apparatus and the monomer collected.

Alkylcyanoacrylate Polymerization

The polymerization of alkylcyanoacrylate monomers can occur by free-radical, anionic or zwitterionic polymerization. (Vauthier, C. et al. "Poly(alkylcyanoacrylates) as biodegradable materials for biomedical applications" Advanced Drug Delivery Reviews 55, pp. 519-548 (2003). For example, an alkyl cyanoacrylate monomer can be polymerized at room temperature without an initiator. The polymerization can be performed in methanol or in an aqueous medium. Polymerization in methanol gives polymers with lower molecular weights and narrower weight distributions. After polymerization, solidified products can be dissolved in acetone and precipitated into an access of methanol to remove residual monomers and other low molecular weight compounds.

PACA polymers having a weight-average molecular weight in the range 75 to 400 kiloDaltons can be prepared by polymerization in aqueous medium. It is believed, but not relied upon for the present invention, that the molecular weight of the PACA polymer can influence the rate of release of the bioactive agent. A slower rate of release is obtained using a polymer of higher molecular weight.

It is also believed, but not relied upon for the present invention, that when an alkylcyanoacrylate monomer is coated onto a medical device using one of the coating methods disclosed below, polymerization occurs before, during, or shortly after, the coating procedure resulting in the coating of a PACA polymer on the surface of the device.

Plasticizers

In certain embodiments of the present invention, a biocompatible plasticizer is coated onto the medical device with the alkylcyanoacrylate monomer. A "biocompatible plasticizer" is any material which is soluble or dispersible in the PACA polymer and that increases the flexibility of the PACA polymer. Plasticizers include, but are not limited to, those described in U.S. Pat. Nos. 2,784,127 and 4,444,933, the contents of both of which are incorporated by reference.

Examples of plasticizers include, but are not limited to, citrates such as triethyl citrate, tri-N-butyl citrate, acetyl trihexyl citrate, N-butyryl tri-N-hexyl citrate, butyryltri-n-hexyl-citrate and acetyltri-n-hexyl citrate, phthalates such as dybutyl phthalate, butyl benxyl phthalate and dioctylphthalate, diethylene glycol dibenzoate, glycol ethers; n-methyl pyrrolidone, 2 pyrrolidone, propylene glycol, glycerol, glyceryl dioleate, ethyl oleate, benzylbenzoate, glycofurol sorbitol, sucrose acetate isobutyrate, sebacates, dipropylene glycol methyl ether acetate, propylene carbonate, propylene glycol laurate, propylene glycol caprylate/caprate, caprylic/capric triglyceride, gamma butyrolactone, polyethylene glycols, vegetable oils including cotton seed oil, soy bean oil, almond oil, sunflower oil peanut oil, and sesame oil, PEG esters of acids and fatty acids, polyglyceryl-3-oleate, polyglyceryl-6-dioleate, polyglyceryl-3-isostearate, PEG-32 glyceryl laurate, PEG-32 glyceryl palmitostearate, PEG-32 glyceryl stearate, glyceryl behenate, cetyl palmitate, glyceryl di stearate, glyceryl tri stearate, glyceryl palmitostearate and glyceryl triacetate.

In one embodiment of the invention, the ratio (wt/wt) of alkylcyanoacrylate monomer to plasticizer is between 5:1 and 1000:1. In another embodiment the ratio (wt/wt) of alkylcyanoacrylate monomer to plasticizer is between 10:1 and 500:1. In yet another embodiment, the ratio (wt/wt) of alkylcyanoacrylate monomer to plasticizer is between 40:1 and 100:1.

Biodegradable Polymers

In certain embodiments of the invention, the medical devices include both a PACA polymer and at least one other biodegradable polymer. For the purposes of this invention, this additional biodegradable polymer will be described as the "biodegradable polymer." Examples of such biodegradable polymers include, but are not limited to, hydrogels (Temenoff, J. S. et al., "Effect of poly(ethylene glycol) molecular weight on tensile and swelling properties of oligo(poly(ethylene glycol)fumarate) hydrogels for cartilage tissue engineering" J. Biomed. Mater. Res. 59, 429-437 (2002), Lee, K. Y. et al. "Controlling mechanical and swelling properties of alginate hydrogels independently by cross-linker type and cross-linking density" Macromolecules 33, 4291-4294 (2000)), elastin-like peptides (van Hest, J. C. M. & Tirrell, D. A., "Protein-based materials, toward a new level of structural control" Chem. Comm. 19, 1897-1904 (2001), Welsh, E. R. & Tirrell, D. A., "Engineering the extracellular matrix: a novel approach to polymeric biomaterials. I. Control of the physical properties of artificial protein matrices designed to support adhesion of vascular endothelial cells" Biomacromolecules 1, 23-30 (2000) and Urry, D. W. et al., "Elastic protein-based polymers in soft tissue augmentation and generation" J. Biomater. Sci., Polym. Ed. 9, 1015-1048 (1998)), and polyhydroxyalkanoates (PHAs) (Poirier, Y. et al., "Production of polyhydroxyalkanoates, a family of biodegradable plastics and elastomers, in bacteria and plants" Bio/Technology 13, 142-150 (1995) and Sodian, R. et al. "Fabrication of a trileaflet heart valve scaffold from a polyhydroxyalkanoate biopolyester for use in tissue engineering" Tissue Eng. 6, 183-187 (2000)).

Suitable biodegradable polymers for use as an additional biodegradable polymer in the present invention include, but are not limited to polylactides (PLA) (including isomers of PLA and combinations thereof), poly(D,L-lactide) (PDLA), poly-L-lactic acid (PLLA), polyglycolides (PGA), poly(ethylene glycol) (PEG), poly(lactide-co-glycolides) (PLGA), polyanhydrides, polyorthoesters, and block copolymers of these compounds. Other suitable biodegradable polymers include, but are not limited to polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(D,L-lactide-co-caprolactone) (PLA/PCL), poly(glycolide-co-caprolactone) (PGA/PCL), poly(phosphate ester), poly(amino acid) and poly(hydroxy butyrate), polydepsipeptides, maleic anhydride copolymers, polyphosphazenes, polyiminocarbonates, poly[(97.5% dimethyl-trimethylene carbonate)-co-(2.5% trimethylene carbonate)], cyanoacrylate, polycyanoacrylates, polyethylene oxide, hydroxypropylmethylcellulose, polysaccharides (such as hyaluronic acid, chitosan and regenerate cellulose), and proteins (such as gelatin and collagen).

Another biodegradable polymer suitable for use in the present invention is poly(glycerolsebacate) (Wang, Y., et al. "A tough biodegradable elastomer" Nature Biotechnology 20, pp. 602-606 (2002)). In one embodiment, such a polymer prepared using about a 1:1 ratio of glycerol/sebacic acid yields a biodegradable polymer capable of large reversible deformations.

Selection of the appropriate biodegradable polymer for use in the present invention depends upon the desired rate of release of the specific bioactive agent, the porosity of the polymer, and the rate of degradation of the polymer, for example. The coating compositions of the present invention may also include additives, such as diluents, carriers, excipients, stabilizers or the like.

Desirably, a biodegradable polymer used in the present invention adequately adheres to the surface of the medical device, and deforms readily after it is adhered to the device. The molecular weight of the polymer(s) should be high enough to provide sufficient toughness so that the polymers will not be rubbed off during sterilization, handling, or deployment of the medical device and will not crack when the device is expanded. The molecular weight of the polymer may be varied to influence the rate of release of the bioactive agent. For example, to obtain a slower rate of release, a polymer(s) of higher molecular weight may be used.

Coating Configurations

In one embodiment of the invention, a bioactive agent is placed directly on the surface of the medical device (or on a primer layer, which is placed directly on the surface of the medical device) and one or more barrier layers are placed over at least a portion of the bioactive agent.

In another embodiment of the invention, the bioactive agent is mixed with a carrier material and this mixture applied to the medical device. In such a configuration, the release of the bioactive agent may be dependent on factors including the composition, structure and thickness of the carrier material. In one embodiment, the carrier material may contain pre-existing channels, through which the bioactive agent may diffuse, or channels created by the release of the bioactive agent, or another soluble substance, from the carrier material.

In other embodiments of the invention, a combination of one or more layers of bioactive agent, mixtures of carrier material/bioactive agent, and barrier layers are present. For example, the bioactive agent may be mixed with a carrier material and coated onto the medical device and then over coated with a barrier layer(s).

In yet other embodiments, multiple layers of bioactive agent, or mixtures of carrier material/bioactive agent, separated by barrier layers are present to form a multicoated medical device. In certain embodiments, different bioactive agents are present in the different layers.

In other embodiments, the bioactive agent forms part of the structure of the medical device itself. Alternatively, the medical device may have holes, wells, slots, grooves, or the like for containing the bioactive agent, and/or mixtures of carrier material/bioactive agent, possibly separated by barrier layers. Illustrative medical devices are disclosed in co-pending U.S. Publication Number 2004-0243225, published Dec. 2, 2004, the contents of which are incorporated by reference. The bioactive agent may be incorporated into a biodegradable medical device that releases the bioactive agent as the device degrades; or the bioactive agent may be incorporated into a medical device in any other known manner. A medical device containing a bioactive agent therein may also include a layer including a bioactive agent, a barrier layer, a layer containing both a bioactive agent and a carrier material, or any combination of these, including combinations including multiple layers.

In the present invention a PACA polymer and, in some embodiments, a biodegradable polymer are present in a carrier material or in a barrier layer. For example, a barrier layer of PACA polymer may be coated onto at least a portion of a layer of bioactive agent and another barrier layer including a biodegradable polymer coated onto at least a portion of the layer of PACA polymer. Alternatively, a mixture of biodegradable and PACA polymers may be coated onto at least a portion of a layer of bioactive agent.

In yet another embodiment, a bioactive agent is mixed with a carrier material and then deposited onto a surface of the medical device. The carrier material can include, for example, a PACA polymer and/or a biodegradable polymer. Optionally, a barrier layer including a PACA polymer and/or a biodegradable polymer may be deposited into the layer containing the bioactive agent and the carrier material.

In one embodiment of the invention, a bioactive agent is coated onto a medical device and a barrier layer containing a PACA polymer coated onto at least a portion of the bioactive agent. A barrier layer of PLA is then coated onto at least a portion of the barrier layer containing the PACA polymer. In one embodiment, the PACA polymer is poly(n-butyl cyanoacrylate).

The present invention also contemplates depositing multiple layers of bioactive compounds, PACA polymers and biodegradable polymers, including layers having different bioactive compounds, PACA polymers and biodegradable polymers, on the medical device. For example, the device may be coated with one or more layers of bioactive agent separated by layers of biodegradable or PACA polymers; layers of bioactive agent separated by layers containing a mixture of biodegradable polymers/PACA polymers; layers of bioactive agent separated by layers containing a mixture of bioactive agent and the biodegradable and/or PACA polymers; layers of the biodegradable and/or PACA polymers separated by layers containing a mixture of bioactive agent and the biodegradable and/or PACA polymers; or with multiple layers of bioactive agent and the biodegradable polymer and the PACA polymer, or any other combination.

In one embodiment of the invention, the ratio of bioactive agent to biodegradable polymer to PACA polymer is varied to control the release of the bioactive agent. In various embodiments of the present invention, the ratio (wt/wt) of biodegradable polymer to the PACA polymer present on or in the medical device is between 400:1 and 1:400, 200:1 and 1:200, 100:1 and 1:100, 20:1 and 1:20, 10:1 and 1:10, 5:1 and 1:5, and 2:1 and 1:2. In various embodiments of the present invention, the ratio (wt/wt) of bioactive agent to the PACA polymer present on or in the medical device is between 400:1 and 1:400, 200:1 and 1:200, 100:1 and 1:100, 20:1 and 1:20, 10:1 and 1:10, 5:1 and 1:5, and 2:1 and 1:2.

Surface Preparation, Optional Layers, and Layer Thickness

In embodiments where the bioactive agent is coated onto a surface of the medical device, it may be advantageous to prepare the surface of the medical device before depositing a coating thereon. Useful methods of surface preparation can include, but are not limited to cleaning; physical modifications such as etching, drilling, cutting, or abrasion; and chemical modifications such as solvent treatment, the application of primer coatings, the application of surfactants, plasma treatment, ion bombardment, covalent bonding and electrochemical methods such as electropolishing, striking, electroplating and electrochemical deposition. Such surface preparation may serve to activate the surface and promote the deposition or adhesion of the coating on the surface. Surface preparation can also selectively alter the release rate of the bioactive agent.

Any additional coating layers can similarly be processed to promote the deposition or adhesion of another layer, to further control the release of the bioactive agent, or to otherwise improve the biocompatibility of the surface of the layers. For example, plasma treating an additional coating layer before depositing a bioactive agent thereon may improve the adhesion of the bioactive agent, increase the amount of bioactive agent that can be deposited, and allow the bioactive agent to be deposited in a more uniform layer.

A primer layer, or adhesion promotion layer, may also be used with the present invention. This layer may comprise, for example, silane, acrylate polymer/copolymer, acrylate carboxyl and/or hydroxyl copolymer, polyvinylpyrrolidone/vinylacetate copolymer (PVP/VA), olefin acrylic acid copolymer, ethylene acrylic acid copolymer, epoxy polymer, polyethylene glycol, polyethylene oxide, polyvinylpyridine copolymers, polyamide polymers/copolymers polyimide polymers/copolymers, ethylene vinylacetate copolymer and/or polyether sulfones.

Coating Methods

The compositions of the present invention may be applied to the medical device in any know manner. For example, a coating may be applied by spraying, dipping, pouring, pumping, brushing, wiping, vacuum deposition, vapor deposition, plasma deposition, electrostatic deposition, ultrasonic deposition, epitaxial growth, electrochemical deposition or any other method known to those skilled in the art.

In one embodiment, the layer of bioactive agent contains from about 0.1 μg to about 100 μg of the bioactive agent per $mm^2$ of the gross surface area of the structure. In another embodiment, the layer of bioactive agent contains from about 1 μg to about 40 μg of the bioactive agent per $mm^2$ of the gross surface area of the structure. "Gross surface area" refers to the area calculated from the gross or overall extent of the structure, and not necessarily to the actual surface area of the particular shape or individual parts of the structure. In other terms, about 100 μg to about 300 μg of bioactive agent per 0.025 mm of coating thickness may be contained on the device surface.

In certain embodiments of the invention, the thickness of each coating layer is between 0.1 μm and 20 μm. In other embodiments, the thickness of each coating layer is between 0.1 μm and 10 μm. In yet other embodiments, the thickness of each coating layer is between 0.1 μm and 5 μm.

The coating of the medical device will now be described using four illustrative methods: spray coating, electrostatic deposition (ESD), ultrasonic deposition (USD) and immersion. However, it will be understood, that the medical device may be coated using any known manner, as well as those mention above.

Spray Coating

In one embodiment, the coating material is dissolved in a solvent(s) and sprayed onto the medical device under a fume hood using a spray gun, such as the Model Number 200 spray gun manufactured by Badger Air-Brush Company, Franklin Park, Ill. 60131. Alignment of the spray gun and medical device may be achieved with the use of laser beams, which may be used as a guide when passing the spray gun up and down the medical device being coated.

In one embodiment of the invention, the coating material is a bioactive agent, for example, an antisense agent, and the solvent about 50% methanol and about 50% chloroform (by volume). Other bioactive agents and solvents may also be used in the present invention.

Electrostatic Spray Deposition

In another embodiment, the coating material is dissolved in a solvent and then sprayed onto the medical device using an electrostatic spray deposition (ESD) process. The ESD process generally depends on the principle that a charged particle is attracted towards a grounded target. Without being confined to any theory, the typical ESD process may be described as follows:

The solution that is to be deposited on the target is typically charged to several thousand volts (typically negative) and the target held at ground potential. The charge of the solution is generally great enough to cause the solution to jump across an air gap of several inches before landing on the target. As the solution is in transmit towards the target, it fans out in a conical pattern which aids in a more uniform coating. In addition to the conical spray shape, the electrons are further attracted towards the conducting portions of the target, rather than towards the non-conductive base the target is mounted on, leaving the coating mainly on the target only.

In the ESD process, the coating solution is forced through a capillary, which is subjected to an electrical field. The solvent mixture leaves the capillary in the form of a fine spray, the shape of which is determined by the electrical field. The medical device is then coated by placing it in the spray and allowing the solvent to evaporate, leaving the desired coating on the surface of the device.

The ESD method allows for control of the coating composition and surface morphology of the deposited coating. In particular, the morphology of the deposited coating may be controlled by appropriate selection of the ESD parameters, as set forth in International Patent Application Serial Number PCT/NL2002/000459, filed Jul. 11, 2002, and published Jan. 23, 2003 as International Publication Number WO 03/006180 (entitled: Electrostatic Spray Deposition (ESD) of biocompatible coatings on Metallic Substrates), the contents of which are incorporated by reference. For example, a coating having a uniform thickness and grain size, as well as a smooth surface, may be obtained by controlling deposition conditions such as deposition temperature, spraying rate, precursor solution, and bias voltage between the spray nozzle and the medical device being coated. The deposition of porous coatings is also possible with the ESD method.

In one embodiment of the invention, the PACA monomer is dissolved in a mixture of two solvents and sprayed onto the medical device using the ESD method. In one embodiment, the solvent mixture comprises about 50% methanol and about 50% chloroform (by volume). In another embodiment, the mixture is about 70% methanol and about 30% dichloromethane (by volume). In another embodiment, the solvent mixture comprises about 50% methanol and about 50% dichloromethane (by volume). In yet another embodiment, the mixture is about 70% methanol and about 30% dichloromethane (by volume).

In one embodiment of the invention, the PACA monomer is n-butyl cyanoacrylate and is dissolved in acetonitrile solvent and sprayed onto the medical device using the ESD method.

Ultrasonic Spray Deposition

In another embodiment, the medical device is coated using an ultrasonic spray deposition (USD) process. Ultrasonic nozzles employ high frequency sound waves generated by piezoelectric transducers which convert electrical energy into mechanical energy. The transducers receive a high frequency electrical input and convert this into vibratory motion at the same frequency. This motion is amplified to increase the vibration amplitude at an atomizing surface.

The ultrasonic nozzle is configured such that excitation of the piezoelectric crystals creates a longitudinal standing wave along the length of the nozzle. The ultrasonic energy originating from the transducers undergoes a step transition and amplification as the standing wave traverses the length of the nozzle. The nozzle is designed such that a nodal plane is located between the transducers. For ultrasonic energy to be effective for atomization, the nozzle tip must be located at an anti-node, where the vibration amplitude is greatest. To accomplish this, the nozzle's length must be a multiple of a half-wavelength. In general, high frequency nozzles are smaller, create smaller drops, and consequently have smaller maximum flow capacity than nozzles that operate at lower frequencies.

Liquid introduced onto the atomizing surface absorbs some of the vibrational energy, setting up wave motion in the liquid on the surface. For the liquid to atomize, the vibrational amplitude of the atomizing surface must be carefully controlled. Below a critical amplitude, the energy is insufficient to produce atomized drops. If the amplitude is excessively high, cavitation occurs. Only within a narrow band of input power is the amplitude ideal for producing the nozzle's characteristic fine, low velocity mist. Since the atomization mechanism relies only on liquid being introduced onto the atomizing surface, the rate at which liquid is atomized depends solely on the rate at which it is delivered to the surface.

For example, the medical device is coated using an ultrasonic spray nozzle, such as those available from Sono-Tek Corp., Milton, N.Y. 12547. The solution is loaded into a 10.0 mL syringe, which is mounted onto a syringe pump and connected to a tube that carries the solution to the ultrasonic nozzle. The syringe pump is then used to purge the air from the solution line and prime the line and spay nozzle with the solution. The stent is loaded onto a stainless steel mandrel in the ultrasonic coating chamber by the following method. In one embodiment, the stent is held on a mandrel by silicone tubing at each end. In this embodiment, the stent does not touch any part of the mandrel, preventing a webbed coating between struts, and the luminal surface is not coated. Alternatively, the stent is attached directly to the mandrel.

In various embodiments, the mandrel had a diameter between 1 mm and 20 mm, preferably between 1 mm and 10 mm. In one embodiment, the stent is 6 mm in diameter and the mandrel's diameter is 3.54 mm. In another embodiment, the stent is 8 mm in diameter and the mandrel's diameter is 4.97 mm. In yet another embodiment, the stent is 10 mm in diameter and the mandrel's diameter is 6.51 mm. Other sized stents and mandrels may also be used in the present invention. The mandrel is fastened onto a motor, positioned below the ultrasonic nozzle. The motor rotates the mandrel at a pre-set speed and translationally moves it so that all parts of the stent pass underneath the ultrasonic spray. In one embodiment, the rotational speed is set to 10 rpm and the translational speed is set to 0.01 mm per second. In another embodiment, the rotational speed is set to 60 rpm and the translational speed is set to 0.05 mm per second. In yet another embodiment, the rotational speed is set to 110 rpm and the translational speed is set to 0.19 mm per second. Other speeds and combinations may also be used in the present invention. The coating chamber is purged with nitrogen to displace oxygen in the system. During the process, the stent is kept at ambient temperature and in a closed chamber.

In one embodiment of the invention, the oxygen concentration is reduced to between 0 and 2000 ppm. In another embodiment the oxygen concentration is reduced to between 200 and 1800 ppm. In yet another embodiment the oxygen concentration is reduced to between 500 and 1500 ppm.

In one embodiment of the invention, the first coating solution contains a bioactive agent, for example, an antisense agent, combined with poly(alkyl cyanoacrylate) monomer, and the second solution contains polylactic acid for over coating. Most preferably, the concentration of the bioactive agent is 4 mg/mL and the concentration of the n-butyl cyanoacrylate is 5 mg/mL. The solvent is about 50% methanol and about 50% chloroform (by volume). The solution is then vortexed for several minutes prior to coating. The concentration of the polylactic acid solution is 4 mg/mL and the solvent is dichloromethane. Other bioactive agents and solvents may also be used in the present invention.

Immersion

In another embodiment, the medical device is immersed into the coating material until the proper thickness is achieved. As the material dries and solidifies it forms the coating layer. Methods for dip coating a medical device are disclosed in, for example, U.S. Pat. No. 6,153,252, issued Nov. 28, 2000, the contents of which are incorporated by reference.

Particle Coating

In another embodiment, a bioactive agent is incorporated into PACA particles and the particles applied to a surface of the implantable medical device. Method of preparing PACA particles containing bioactive compounds are known to those skilled in the art. For example, such methods are described in: Zimmer, A., "Antisense Oligonucleotides Delivery with Polyhexylcyanoacrylate Nanoparticles as Carriers", Methods: A Companion to Methods in Enzymology 18, pp 288-295 (1999); Fontana, G. et al., "Amoxicillin-loaded polyethylcyanoacrylate nanoparticles: Influence of PEG coating on the particle size, drug release rate and phagocytic uptake" Biomaterials 22, pp. 2857-65 (2001) and Li, S. et al., "In vitro release of protein from poly(butylcyanoacrylate) nanocapsules with an aqueous core" Colloid Poly Sci 283, pp 480-85 (2005)

For the purposes of the invention, the size of the particle is the largest cross-sectional dimension of the particles. In one embodiment of the present invention, particles incorporating bioactive compounds have a size of between 10 and 1000 nm. In another embodiment, the particles have a size of between 100 and 1000 nm. In yet another embodiment, the particles have a size of between 200 and 500 nm.

Particles incorporating a bioactive compound may be applied to a medical device by any of the methods discussed above. In one embodiment, the particles are applied to the medical device and are over coated by a biodegradable polymer.

Sterilization Procedure Prior to Implantation

The medical devices of the present invention may require sterilization prior to implantation into the body. In one embodiment, the medical device is loaded into final packaging, and gamma irradiated in a gamma chamber. In one embodiment, the implantable medical device is irradiated with between 1 and 100 kGy. In another embodiment, the implantable medical device is irradiated with between 5 and 50 kGy, and in yet another embodiment, the implantable medical device is irradiated with between 25 and 28 kGy.

Bioactive Agent Elution Profile The bioactive agent elution profile of a medical device comprising a bioactive agent can be obtained by any suitable method that allows for measurement of the release of the bioactive agent in a manner that can be measured with a desired level of accuracy and precision. In one embodiment, the elution profile of the release of a bioactive agent is obtained by contacting the medical device with a suitable test solution. The test solution can be configured to simulate conditions believed to be present at a particular point of treatment within a body vessel. For example, a test solution comprising bovine serum can be used to simulate implantation within a blood vessel. The release of bioactive agent from the medical device can be measured by any suitable spectrographic method, such as measurement of a UV absorption spectrum of the test fluid after contacting the medical device.

The amount of bioactive agent on the medical device can be determined by contacting the medical device with a suitable solvent and detecting the amount of bioactive agent released from the medical device into the solvent. A suitable solvent solubilizes a bioactive agent while allowing for subsequent measurement of the solubilized bioactive agent in a manner that can be correlated to the amount of bioactive agent released from the medical device. In one embodiment, the solvent is selected to quickly solubilize the bioactive agent. Optionally, the solvent may dissolve the bioactive agent more aggressively than the test solution. Preferably, substantially all the bioactive agent is removed from the medical device after contact with the solvent. The bioactive agent can then be subsequently detected and the detection of the bioactive agent can be correlated to the amount of bioactive agent that was present on the medical device surface prior to contacting the medical device with the solvent.

In one embodiment, the elution profile of a bioactive agent from a medical device is determined by first contacting the medical device with a test solution and then subsequently detecting the amount of bioactive agent within the test solution. The medical device is exposed to the test solution and the rate of release of the bioactive agent from the medical device is determined by detecting the bioactive agent in the test solution for a first desired period of time. After the first desired period of time, the amount of bioactive agent remaining on the medical device can be determined by contacting the medical device with a suitable solvent, and subsequently detecting the amount of bioactive agent leaving the medical device in the solvent.

One or more suitable analytical techniques may be used to detect a bioactive agent. A suitable method, such as a spectrographic technique, permits measurement of a property of the test solution that can be correlated to the presence or concentration of the bioactive agent with a desired level of accuracy and precision.

In one embodiment, absorption spectroscopy can be used to detect the presence of a bioactive agent, such as in a test solution or solvent solution. Accordingly, the Beer-Lambert Correlation may be used to determine the concentration of a bioactive agent in a solution. This correlation involves the linear relationship between absorbance and concentration of an absorbing species. Using a set of standard samples with known concentrations, the correlation can be used to measure the absorbance of the sample. A plot of concentration versus absorbance can then be used to determine the concentration of an unknown solution from its absorbance.

Bioactive Agents

Suitable bioactive agents for use in the present invention may include, but are not limited to heparin, covalent heparin, or another thrombin inhibitor, hirudin, hirulog, argatroban, D-phenylalanyl-L-poly-Larginyl chloromethyl ketone, or another antithrombogenic agent, urokinase, streptokinase, a tissue plasminogen activator, or another thrombolytic agent, 17-beta estradiol (estrogen), absorbable Mg-alloy, ABT 578, actinomycin D, Batimastat (a metalloproteinase inhibitor), Endothelial progenitor cells (EPC) (surface antibodies), Myfortic® (Mycophenolic acid (MPA) sodium), antisense drugs such as RESTEN-NG® (NEUGENE® drugs), paclitaxel (TAXOL®) and other taxane derivatives, Biolimus A7, BIOLIMUS A9™, everolimus, sirolimus (rapamycin), pimecrolimus, or any other member of the -olimus family, a fibrinolytic agent, a vasospasm inhibitor, a calcium channel blocker, a nitrate, nitric oxide, a nitric oxide promoter or another vasodilator, HYTRIN® or other antihypertensive agents, an antimicrobial agent or antibiotic, aspirin, ticlopidine, a glycoprotein IIb/IIIa inhibitor or another inhibitor of surface glycoprotein receptors, or another antiplatelet agent, colchicine or another antimitotic, or another microtubule inhibitor, dimethyl sulfoxide (DMSO), a retinoid or another antisecretory agent; cytochalasin or another actin inhibitor, or a remodelling inhibitor, deoxyribonucleic acid, an antisense nucleotide or an other agent for molecular genetic intervention, methotrexate or another antimetabolite or antiproliferative agent, tamoxifen citrate, PROSCAR®, HYTRIN®, EULEXIN®, or the derivatives thereof, or other anti-cancer chemobioactive agents, dexamethasone, dexamethasone sodium phosphate, dexamethasone acetate or another dexamethasone derivative, or another anti-inflammatory steroid or non-steroidal antiinflammatory agent, cyclosporin or another immunosuppressive agent, trapidal (a PDGF antagonist), angiopeptin (a growth hormone antagonist), angiogenin, a growth factor or an anti-growth factor antibody, or another growth factor antagonist, dopamine, bromocriptine mesylate, pergolide mesylate or another dopamine agonist, $^{60}$Co (5.3 year half life), $^{192}$Ir (73.8 days), $^{32}$P (14.3 days), $^{111}$In (68 hours), $^{90}$Y (64 hours), $^{99m}$Tc (6 hours) or another radiobioactive material, iodine-containing compounds, barium-containing compounds, gold, tantalum, platinum, tungsten or another heavy metal functioning as a radiopaque agent, a peptide, a protein (e.g. a viral protein), an enzyme, an extracellular matrix component, a cellular component or another biologic agent, captopril, enalapril or another angiotensin converting enzyme (ACE) inhibitor, ascorbic acid, alpha tocopherol, superoxide dismutase, deferoxamine, a 21-aminosteroid (lasaroid) or another free radical scavenger, iron chelator or antioxidant, a $^{14}$C-, $^{3}$H-, $^{131}$I-, $^{32}$P- or $^{36}$S-radiolabelled form or other radiolabelled form of any of the foregoing, estrogen or another sex hormone, AZT or other antipolymerases, acyclovir, famciclovir, rimantadine hydrochloride, ganciclovir sodium, NORVIR®, CRIXIVAN®, or other antiviral agents, 5-aminolevulinic acid, meta-tetrahydroxyphenylchlorin, hexadecafluoro zinc phthalocyanine, tetramethyl hematoporphyrin, rhodamine 123 or other photodynamic therapy agents, an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin or other antibody targeted therapy agents, gene therapy agents, and enalapril and other prodrugs, PROSCAR®, HYTRIN® or other agents for treating benign prostatic hyperplasia (BHP) or a mixture of any of these, and various forms of small intestine submucosa (SIS).

A wide variety of known immunosuppressive agents are expected to be useful as bioactive agents in the practice of the present invention. More specifically, useful immunosuppressive agents include azathioprine or azathioprine sodium, an imidazoyl derivative of 6-mercaptopurine (6-MP) and its sodium salt, basiliximab, a chimeric (murine/human) monoclonal antibody, in particular, an interleukin-2 (IL-2) receptor antagonist or anti-interleukin-2 receptor (CD25) antibody, cyclosporin or cyclosporine (cyclosporin A), a cyclic polypeptide consisting of 11 amino acids, produced as a metabolite of the fungus species Beauveria nivea (Tolypocladium inflatum Gams, daclizumab (dacliximab), a humanized $IgG_1$ monoclonal antibody produced by recombinant DNA technology that binds specifically to the alpha subunit (Tac subunit) of the human high-affinity interleukin-2 (IL-2) receptor (anti-interleukin-2-receptor antibody), a composite of 90% human and 10% murine antibody sequences, glatiramer or glatiramer acetate, a random synthetic copolymer of L-alanine, L-glutamic acid, L-lysine and L-tyrosine, in a molar ratio of 6:1.9:4.7:1, and its acetate, muromonab-CD3, a murine monoclonal antibody to the T3 (CD3) antigen of human T-cells, more particularly, a biochemically purified $IgG_{2a}$ immunoglobulin; mycophenolate, mycophenolate mofetil (MMF), mycophenolate morpholinoethyl or mycophenolic acid (mycophenolate hydrolyzes to form an active metabolite (MPA), a potent, selective, uncompetitive and reversible inhibitor of inosine monophosphate dehydrogenase, mycophenolic acid is derived from Penicillium stoloniferum), tacrolimus (FK506), anhydrous tacrolimus or tacrolimus monohydrate, a macrolide immunosuppressant produced by Streptomyces tsukubaensis which inhibits T-lymphocyte activation, sirolimus, a macrolide immunosuppressive agent also obtained from Streptomyces tsukubaensis which inhibits both T-lymphocyte activation and proliferation that occurs in response to antigenic and cytokine (interleukin [IL]-2, IL-4 and IL-5) stimulation, and also inhibits antibody production, interferon alfa-2a, recombinant (rIFN-A or IFLrA), a highly purified, sterile protein containing 165 amino acids, manufactured by recombinant DNA technology that employs a genetically engineered Escherichia coli bacterium, antilymphocyte immunoglobulin (ALG) or antithymocyte immunoglobulin (ATG), polyclonal antibodies to human lymphocytes produced by the purification of sera from appropriately immunized animals such as horses, rabbits and goats (ALG implies a product raised against all lymphocyte subsets, while ATG implies specificity for T-cells, either thymus lymphocytes or thymocytes), as well as their native sera (antilymphocyte serum and antithymocyte serum, respectively, sometimes referred to as lymphocytic antiserum and thymitic antiserum, respectively), brequinar or brequinar sodium, an inhibitor of pyrimidine metabolism, cyclophosphamide, cyclophosphamide monohydrate or anhydrous cyclophosphamide, an antineoplastic that is converted in the body to an active alkylating metabolite with properties similar to those of mustine, dactinomycin, actinomycin C, actinomycin D or meractinomycin, an antibiotic produced by the growth of Streptomyces chrysomallus and other species of Streptomyces, daunorubicin, daunorubicin hydrochloride, daunomycin hydrochloride or rubidomycin hydrochloride, an antineoplastic anthracycline antibiotic produced by Streptomyces coeruleorubidus or S. peucetius, and its hydrochloride, doxorubicin, doxorubicin hydrochloride, adriamycin or adriamycin hydrochloride, an anthracycline antineoplastic antibiotic isolated from certain strains of Streptomyces coeruleorubidus or S. peucetius, and its hydrochloride, fluorouracil, a pyrimidine analogue, in particular an antineoplastic that acts as an antimetabolite to uracil, gusperimus or gusperimus hydrochloride, a guanidine derivative and its hydrochloride, inolimomab, a murine antihuman monoclonal antibody directed against the alpha-chain of the interleukin-2 receptor (CD25), leflunomide, having immunosuppressant properties believed to be partly due to the action of its active metabolite A77-1726 in inhibiting pyrimidine synthesis; mercaptopurine, mercaptopurine monohydrate, purinethiol or anhydrous mercaptopurine, an antineoplastic that acts as an antimetabolite, methotrexate, methotrexate sodium, methotrex ate disodium, alpha-methopterin or amethopterin, a mixture of 4-amino-10-methylfolic acid and related substances, or the sodium salts thereof, acting as an antimetabolite of folic acid, mustine, mustine hydrochloride, chlormethine hydrochloride, chlorethazine hydrochloride, mechlorethamine hydrochloride or nitrogen mustard (mustine), an alkylating agent, mizoribine, 5-hydroxy-1-beta-D-ribofuranosylimidazole-4-carboxamide, vinblastine, vinblastine sulfate or vincaleukoblastine sulphate, an alkaloid (vincaleukoblastine) extracted from Vinca rosea (Catharanthus roseus) (Apocynaceae), or a sulfate thereof, pharmacologically or physiologically acceptable salts of any of the foregoing and pharmacologically or physiologically acceptable mixtures of any two or more of the foregoing.

Water-Soluble Bioactive Agents

In one embodiment of the present invention, the bioactive agent is water-soluble. For the purposes of this invention, the solubility of the bioactive agent in determined at standard atmospheric pressure and at 25° C. In one embodiment, the bioactive agent has a solubility of greater that 0.5 g/l in water. In another embodiment, the bioactive agent has a solubility of greater that 2.5 g/L in water. In yet another embodiment, the bioactive agent has a solubility of greater that 10 g/L in water. In yet another embodiment, the bioactive agent has a solubility of greater that 25 g/L in water. In yet another embodiment, the bioactive agent has a solubility of greater that 50 g/L in water.

Suitable water-soluble bioactive agents for use in the present invention may include, but are not limited to antisense agents such as NeuGene antisense agents, Adrenergics such as Oxymetazoline HCl, Norfenefrine HCl and Bretylium Tosylate; Adrenergic agonists such as Ephedrine; Adrenergic antagonists such as Moxisylyte HCl; Adrenocorticotropic hormones such as Corticotropin; Analgesics such as Pseudophedrine hydrochloride, Acetominophen, Chlorpheniramine Maleate, Hydroxypethidine HCl and Norpipanone HCl & HBr; Anesthetics such as Dyclonine HCl, Hydroxydione Sodium and Acetamidoeugenol; Anthelmintics such as Nitroxynil N-ethylglucamine, Anthiolimine and 8-Hydroxyquinoline Sulfate; Anti-inflammatory agents such as Amiprilose HCl, Balsalazide Disodium Salt and Benzydamine HCl; Antiallergics such as Pemirolast Postassium salt, Cromolyn Disodium salt and Nedocromil Disodium salt; Antianemics such as Calcium Folarin and Calcium folinate; Antianginals such as Acebutolol HCl, Bufetolol HCl and Timolol Hydrogen maleate salt; Antiarryhythmics such as Encamide HCl, Bretylium Tosylate and Butobendine Dichloride; Antiarthritics such as Glucosamine Beta Form and Actarit; Antiasthmatics/Leukotriene antagonists such as Cromalyn Disodium; Halamid and Montelukast Monosodium salt; Antibiotics such as Gentamicin, Erythromycin and Azithromycin; Antibacterials such as Cefoxitin Sodium salt, Lincolcina and Colisitin sulfate; Anticoagulants such as Heprin sodum salt, Heparin Sodium and Dextran Sulfate Sodium; Anticonvulsants such as Paramethadione (Paradione), Phenobarbital sodium salt and Levetiracetam; Antidepressants such as Fluoxetine HCl, Paroxetine and Nortiptyline HCl; Antidiabetics such as Glucobay/Prandase/Precose, Human Insulin, Insulin Aspart and Mefformin Hydrochloride; Antiemetics such as Chlorpromazine HCl, Cyclizine HCl and Dimenhydrinate; Antiglaucoma agents such as Dorzolamide HCl, Epinepherine (all forms) and Dipivefrin HCl; Antihistamines such as Histapyrrodine HCl; Antihyperlipoproteinemics such as Pantethine (Lipodel); Antihypertensives such as Atenolol, Guanabenz Monoacetate, Hexamethonium (Br, Cl, I, and Tartrate) and Hydroflumethiazide; Antihypotensive such as Cortensor (Heptaminol HCl), Pholedrine Sulfate and Norepinephrine HCl; Antimalarials such as Amodiaquin Dihydrochloride dehydrate, Bebeerine HCl and Chloroquine Diphosphate; Antimigraine agents such as Eletriptan Hydrobromide (Relpax), Valproic Acid Sodium salt and Dihydroergotamine mesylate; Antineoplastics such as L-Asparaginase w/PEG, Bleomycins, Peplomycin Sulfate salt, Tallysomycin A, Vincaleukoblastine Sulfate, Carboplatin, Capecitabine, Cisplatin, Doxorubicin HCl, Carcinil and Nipent; Antiparkinsons agents such as Amantadine HCl, Ethylbenzhydramine HCl and Scopolamine N-Oxide Hydrobromide; Antiperistaltics such as Diphenoxylate HCl; Antiprotozoals such as Aeropent, Pentamideine Isethionate and Oxophenarsine Hydrochloride; Antipsycotics such as Haloperidol HCl, Triflupromazine HCl and Trifluperidol HCl; Antipyretics such as Imidazole Salicylate, Lysine Acetylsalicylate and Magnesium Acetylsalicylate; Antirheumatics such as Penicillamine HCl, Chloroquine Diphosphate, Gold Sodium Thiomalate and Hydroxychloroquine Sulfate; Antispasmodics such as Ethaverine HCl, Fenpiverinium Bromide and Leiopyrrole HCl; Antithrombotics such as Ticlopidine HCl; Antitussives such as Amicibone HCl, Butethamate Citrate and Carbetapentane Citrate; Antiulcer agents such as Ranitidine HCl, Pirenzepine 2 HCl and Misoprostol; Antiviral agents such as Acyclovir, Glanciclovir, Penciclovir, Rimantadine HCl, Valacyclovir HCl and Epivar; HIV I Protease Inhibitors such as Crixivan; Anxiolytics such as Flesinoxan HCl, Chlordiazepoxide HCl and Clorazepic Acid Dipotassium salt; Broncodialtors such as Dypylline, Eprozinol 2HCl and Etafedrine; Bronchodilators/Antiarrhythmics such as Ipratropium Bromide; Cardiotonics such as Digitalin (Diginorgin), Dopamine HCl and Heptaminol HCl; Cholinergics such as Methacholine Chloride, Methacholine Chloride, Edrophonium chloride, Antilirium, Juvastigmin (Neostigmine Bromide) and Intrastigmina; Cholinergic Antagonists such as Penthienate bromide, Pehencarbamide HCl, Glycopyrrolate and Hyoscyamine Sulfate dehydrate; Cognition enhancers/Nootropics such as Tacrine HCl, Aceglutamide Aluminum Complex and Acetylcarnitine L HCl; Degongestants such as Cyclopentamine HCL, Fenoxazoline HCl and Naphazoline HCl; Diagnosit aids such as Diatrizoate sodium and Meglumine Diatrizoate; Diuretics such as Amiloride HCl $2H_2O$ and Manicol, Urea; Fungicides such as Amphotericin B, Caspofungin Acetate and Viridin; Gonad stimulating principle such as Chorionic gonadotropin, Humegon and Luteinizing hormone (LH); Hemorheologic agents such as Azupentat; Hemostatics such as 6-Aminohexanoic acid, Factor IX and Carbazochrome Salicylate; Hypolimpemic agents such as Clofibric Acid Magnesium salt, Dextran Sulfate Sodium and Meglutol; Immunosuppresants such as Brequinar Sodium salt (DUP-785), Gusperimus Trihydrochloride and Mizoribine; Mydriatics; antispasmodics such as Atropine Methylnitrate, Atropine Sulfatemonohydrate and Hydroxyamphetamine (I, HCl, HBr); Neuromuscular blocking agent/Muscle Relaxants (Skeletal) such as Pancuronium Bromide, Doxacurium Chloride and Pancuronium bromide); Oxytocics such as Intertocine-S, Ergonovine Maleate and Prostoglandin $F_{2\alpha}$ Tromethamine salt); Sedatives/Hypnotics such as Pentaerythritol Chloral, Diethylbromoacetamide and Barbital Sodium salt; Serenics such as Eltoprazine (DU-28853); Tocolytic agents such as Albuterol Sulfate; Terbutaline sulfate; Vasoconstrictors such as Nordefrin HCl; Peripheral Vasodilators such as Pentoxifylline, Diazeniumdiolates and Diisopropylamine dichloroacetate; Cerebral Vasodilators such as Citicoline and Fasudil HCl; Coronary Vasodilators such as Hexestrol Bis(β-diethylaminoethyl ether) 2HCl and Hexobendine 2HCl; Enzyme inhibitors (proteinase) such as Gabexate Methanesulfonate; Radioprotective agents such as Amifostine $3H_2O$; Vitamins such as Pantothenic Acid sodium salt; and other agents such as Uridine 5'-Triphosphate Trisodium dihydrate salt.

Antisense Compounds

In one embodiment of the present invention, the bioactive agent is an antisense compound. Such compounds are useful as research reagents, diagnostic aids and in the treatment of the many human diseases that arise from the increased function of genes within the body. It is believed, but not relied upon for the present invention, that antisense compounds act by binding tightly to nucleic acid sequences responsible for the expression of disease-related proteins and hence preventing or reducing the expression of such proteins.

Early antisense compounds were made up of natural nucleic acid oligonucleotides consisting of a phosphate/sugar backbone and nucleic acid bases attached to the backbone. Later compounds contained modified backbones that were designed to resist degradation by enzymes and to enter tissues and cells more efficiently. Examples of antisense compounds containing a modified backbone include the NEUGENE® antisense compounds (available from AVI BioPharma Portland, Or). Such compounds contain a morpholino backbone and highly water soluble, have resistance to breakdown by nucleases and have low production costs. For example, U.S. Pat. No. 7,094,765B1, issued Aug. 22, 2006, the contents of which are incorporated by this reference, describes a morpholino antisense compound for use in the treatment of restenosis. This antisense compound has uncharged phosphorus-containing backbone linkages and a sequence of nucleotide bases spanning the start codon of human c-myc mRNA.

Applications for antisense compounds include use in drug metabolism and in treating cardiovascular disease, cancer, polycystic kidney disease, and viral diseases. In particular, the Resten-NG, and Resten-MP antisense compounds (AVI BioPharma Portland, Oreg.) have applications in the treatment of restenosis.

In one embodiment of the present invention, an antisense compound having application to the treatment of restenosis, for example, the RESTEN-NG, antisense compound, is attached to a vascular stent for delivery to a treatment site within the vascular system. In such an application, it is important that the antisense compound remains attached to the stent until delivery to the treatment site and is then released over a time period compatible with the treatment regime.

Problems arise because the high water solubility of many antisense compounds can result in the release of all or most of the antisense compound before delivery to the required site of treatment. Even if sufficient antisense compound remains on the stent after delivery, the release of a substantial proportion of this compound before delivery results in the need to incorporate higher a dosage of the compound onto the stent that would otherwise be required.

One embodiment of the present invention provides a stent having coatings of the antisense compound, a biodegradable polymer and a PACA polymer. Such coatings may be applied such that the antisense compound and the polymers are present as separate layers. Alternatively, two or more of these compounds may be present in the same layer.

Medical Devices

Medical devices of the present invention include, but are not limited to, stents, stent grafts, vascular grafts, catheters, guide wires, balloons, filters (e.g. vena cava filters), intraluminal paving systems, sutures, staples, anastomosis devices, vertebral disks, bone pins, suture anchors, hemostatic barriers, clamps, screws, plates, clips, vascular implants, tissue adhesives and sealants, tissue scaffolds, valves (e.g. venous valves), abdominal aortic aneurysm (AAA) grafts, embolic coils, various types of dressings, bone substitutes, intraluminal devices, vascular supports, or other known bio-compatible devices. The medical devices of the present invention may be placed in the coronary vasculature, esophagus, trachea, colon, bladder, heart, vessels, lumens, intestines, biliary tract, urinary tract, prostate, or brain, for example.

In one embodiment of the present invention, the medical device comprises an intraluminal stent. The stent may be self-expanding or balloon-expandable and may be a bifurcated stent, a coronary vascular stent, a urethral stent, a ureteral stent, a biliary stent, a tracheal stent, a gastrointestinal stent, or an esophageal stent, for example. More specifically, the stent may be, for example, a Wallstent variety stent or a Gianturco-Roubin, Palmaz-Shatz, Wiktor, Strecker, Cordis, AVE Micro Stent, Igaki-Tamai, Millenium Stent, Steeplechaser stent (Johnson & Johnson), Cypher (Johnson & Johnson), Sonic (Johnson & Johnson), BX Velocity (Johnson & Johnson), Flexmaster (JOMED) JoStent (JOMED), S7 Driver (Medtronic), R-Stent (Orbus), Technic stent (Sorin Biomedica), BiodivYsio (Abbott Laboratories), DuraFlex (Avantec Vascular), NIR stent (Boston Scientific), Express 2-stent (Boston Scientific), Liberte stent (Boston Scientific), Achieve (Cook/Guidant), S-Stent (Guidant), Vision (Guidant), or Multi-Link (Guidant). Some exemplary stents are disclosed in U.S. Pat. Nos. 5,292,331 to Boneau, 6,090,127 to Globerman, 5,133,732 to Wiktor, and 4,739,762 to Palmaz, 5,421,955 to Lau. Desirably, the stent is a vascular stent such as the commercially available Gianturco-Roubin FLEX-STENT®, GRII™, SUPRA-G, or V FLEX coronary stents from Cook Incorporated (Bloomington, Ind.).

Such stents are typically about 10 to about 60 mm in length and designed to expand to a diameter of about 2 to about 6 mm when inserted into the vascular system of the patient. The Gianturco-Roubin stent in particular is typically about 12 to about 25 mm in length and designed to expand to a diameter of about 2 to about 4 mm when so inserted.

These stent dimensions are, of course, applicable to exemplary stents employed in the coronary arteries. Structures such as stents or catheter portions intended to be employed at other sites in the patient, such as in the aorta, esophagus, trachea, colon, biliary tract, or urinary tract will have different dimensions more suited to such use. For example, aortic, esophageal, tracheal and colonic stents may have diameters up to about 25 mm and lengths about 100 mm or longer.

The structure of the stent is composed of a base material suitable for the intended use of the structure. The base material is preferably biocompatible, although cytotoxic or other poisonous base materials may be employed if they are adequately isolated from the patient. Such incompatible materials may be useful in, for example, radiation treatments in which a radioactive material is positioned by catheter in or close to the specific tissues to be treated. Under most circumstances, however, the base material of the structure should be biocompatible.

A variety of conventional materials can be employed as the base material. Some materials may be more useful for structures other than the coronary stent exemplifying the structure. The base material may be either elastic or inelastic, depending upon the flexibility or elasticity of the polymer layers to be applied over it. The base material may be either biodegradable or non-biodegradable, and a variety of biodegradable polymers are known. Moreover, some bioactive agents have sufficient strength to serve as the base material of some useful structures, even if not especially useful in the exemplary coronary stent.

The materials used in stent or other medical device of the invention may be selected from a well-known list of suitable metals and polymeric materials appropriate for the particular application, depending on necessary characteristics that are required (self-expansion, high radial force, collapsibility, etc.). Suitable metals or metal alloys include stainless steels (e.g., 316, 316L or 304), nickel-titanium alloys including shape memory or superelastic types (e.g., nitinol or elastinite); inconel; noble metals including copper, silver, gold, platinum, paladium and iridium; refractory metals including Molybdenum, Tungsten, Tantalum, Titanium, Rhenium, or Niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; bioabsorbable materials, including magnesium; or other biocompatible metals and/or alloys thereof.

One particularly preferred material is a self-expanding material such as the superelastic nickel-titanium alloy sold under the tradename NITINOL. Materials having superelastic properties generally have at least two phases: a martensitic phase, which has a relatively low tensile strength and which is stable at relatively low temperatures, and an austenitic phase, which has a relatively high tensile strength and which can be stable at temperatures higher than the martensitic phase. Shape memory alloys undergo a transition between an austenitic phase and a martensitic phase at certain temperatures. When they are deformed while in the martensitic phase, they retain this deformation as long as they remain in the same phase, but revert to their original configuration when they are heated to a transition temperature, at which time they transform to their austenitic phase. The temperatures at which these transitions occur are affected by the nature of the alloy and the condition of the material. Nickel-titanium-based alloys (NiTi), wherein the transition temperature is slightly lower than body temperature, are preferred for the present invention. It can be desirable to have the transition temperature set at just below body temperature to insure a rapid transition from the martinsitic state to the austenitic state when the frame can be implanted in a body lumen.

In one embodiment, the medical device comprises a self-expanding nickel titanium (NiTi) alloy material. The nickel titanium alloy sold under the tradename NITINOL is a suitable self-expanding material that can be deformed by collapsing the frame and creating stress which causes the NiTi to reversibly change to the martensitic phase. The frame can be restrained in the deformed condition inside a delivery sheath typically to facilitate the insertion into a patient's body, with such deformation causing the isothermal phase transformation. Once within the body lumen, the restraint on the frame can be removed, thereby reducing the stress thereon so that the superelastic frame returns towards its original undeformed shape through isothermal transformation back to the austenitic phase. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," Scientific American, 281: 74-82 (November 1979), incorporated herein by reference.

Some embodiments provide medical devices that are not self-expanding, or that do not comprise superelastic materials. For example, in other embodiments, the medical device can comprise silicon-carbide (SiC). For example, published U.S. Patent Application Number US2004/034409 to Hueblein et al., published on Feb. 14, 2004 and incorporated in its entirety herein by reference, discloses various suitable materials and configurations.

Other suitable materials used in the medical device includes carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these.

The medical device may be deployed according to conventional methodology, such as by an inflatable balloon catheter, by a self-deployment mechanism (after release from a catheter), or by other appropriate means. The medical device may be formed through various methods, such as welding, laser cutting, or molding, or it may consist of filaments or fibers that are wound or braided together to form a continuous structure. The medical device may be a grafted stent in which the bioactive agent is incorporated into the graft material.

Of course, when the structure is composed of a radiolucent material such as polypropylene, polyethylene, or others above, a conventional radiopaque coating may and preferably should be applied to it. The radiopaque coating provides a means for identifying the location of the structure by X-ray or fluoroscopy during or after its introduction into the patient's vascular system.

Methods of Delivery and Treatment

Another aspect of the invention provides a method of treatment involving inserting into a patient or non-human subject an implantable medical device having any of the novel configurations described above and delivering one of the bioactive agents described above to the body of the patient or non-human subject. For example, when the implantable medical device is a stent coated by the coating methods described above, the method of treatment involves implanting the stent into the vascular system of a patient and allowing the bioactive agent(s) to be released from the stent in a controlled manner, as could be shown by the drug elution profile of the coated stent.

The dosage level and period of release of the bioactive agent may be tailored to the subject being treated, the severity of the affliction, the judgment of the physician, and the like. In one embodiment of the invention, a vascular stent is coated with a drug at a concentration of 0.1-4 $\mu g/mm^2$. In another embodiment, the stent is coated with a drug at a concentration of 0.1-2 $\mu g/mm^2$. In yet another embodiment, the stent is coated with a drug at a concentration of 0.1-1 $\mu g/mm^2$.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as herein before set forth can be made without departing from the spirit and scope thereof, and, therefore, only such limitations should be imposed as are indicated by the appended claims.

EXAMPLES

Comparative Example 1

Elution of a Water-Soluble Drug from a Stent not Having a Polymer Coating

6×20 mm Zilver stents are available from Wilson-Cook, Bloomington, Ind. Resten-NG™ antisense drug (product number 4126) is available form AVI BioPharma, Corvallis, Oreg. 97333. Four Zilver stents were cleaned in methanol and preweighed on a microgram balance. A solution containing 40 mg of antisense drug in 10 ml of 50:50 $CHCl_3$/MeOH was placed in an electrostatic coating machine (Terronics Development Corporation, Elwood, Ind. 46036) and the stent coated for 2 minutes at a flow rate of 0.03 ml/min. Each stent was then dried and weighed again. About 94 µg of antisense drug was determined to be coated onto each stent.

Each stent was added to 10.5 ml of distilled water. After three inversions, a 1 ml sample of the liquid was removed and the UV spectrum measured using an Agilent UV spectrometer at 257 nm wavelength. After measurement, the sample was returned and to the original solution. This process was repeated and UV spectra obtained after exposure times of 9, 48, 112, 210, 363 and 450 seconds.

A maximum optical density was observed at 257 nm. Results indicated that substantially all the antisense drug was eluted from the stent within 1 minute of exposure to the aqueous environment.

Comparative Example 2

Elution of a Water-Soluble Drug from a Stent Having a PLA Overcoat

Three Zilver stents were coated with a solution of 4 mg/ml antisense drug using the procedure of Example 1. The amount of antisense drug coated onto each stent was determined by weighing the stents before and after coating and is shown in Table 1. The stents were then over coated with PLA (Sigma-Aldrich Corporation, St Louis, Mo.) by spray coating a 4 mg/ml solution of PLA in dichloromethane (Sigma-Aldrich Corporation, St Louis, Mo.).

Before coating, a Badger No. 200 spray gun (Badger Air-Brush, Company, Franklin Park, Ill.), was calibrated to a flow rate of 5.8 ml/min. Stent 1 was sprayed from four sides. 20 ml of PLA solution was sprayed at each position. For stents 2 and 3, the coating conditions were the same except that 30 ml of PLA solution was used at each spray position. After coating, the stents were again weighed. The amount of PLA coated onto each stent is shown is Table 1.

After coating, the elution time of the antisense drug was determined using the UV analysis method of Example 1. Table 1 shows the time taken for 90 percent of the coated antisense drug to elute from each stent.

TABLE 1

| Stent | Antisense Drug (μg) | PLA (μg) | 90% elution time (min.) |
|---|---|---|---|
| 1 | 196 | 280 | 8 |
| 2 | 237 | 441 | 9.6 |
| 3 | 278 | 497 | 14.5 |

Example 1

Elution of a Water-Soluble Drug from a Stent Having a PLA and a PACA Overcoat

Three Zilver stents were coated with antisense drug and then with PLA using the protocol described in Example 2. Table 2 shows the amounts of antisense drug and PLA coated onto each stent. N-butyl cyanoacrylate monomer (NBCA) containing 10% Tri Butyl Citrate (plasticizer) and trace amounts of Butyl Hydroxyanisole and Sulphur Dioxide (stabilizers), (Glustitch, Inc., Washington 98281) was then applied to each stent using the method of Example 1. The coating solution contained 2.5 mg/ml NBCA in acetonitrile. The coating times were 40, 60 and 120 seconds for stents 1, 2 and 3 respectively. Table 2 shows the amount of NBCA coated onto the stents.

After coating, the elution time of the antisense drug was determined using the UV analysis method of Example 1. Table 2 shows the time taken for 90 percent of the coated antisense drug to elute from each stent.

TABLE 2

| Stent | Antisense Drug (μg) | PLA (μg) | n-butyl cyanoacrylate (μg) | 90% elution time (min.) |
|---|---|---|---|---|
| 1 | 277 | 91 | 43 | 2.8 |
| 2 | 255 | 85 | 92 | 9.5 |
| 3 | 254 | 90 | 140 | 23.8 |

Example 2

Coating Using an Ultrasonic Coating Method

A mixture containing 4 mg/ml Resten-NG™ antisense drug and 8 mg/ml NBCA was prepared on 50:50 MeoH:CHCl$_3$. The solution was loaded into a syringe mounted onto a syringe pump and connected to a tube that carried the solution to the ultrasonic nozzle (Sonotek, Milford, Conn. 06460). Air was purged from the solution line and the spray nozzle primed with the solution. The coating chamber was purged with nitrogen to attain an oxygen concentration of between 500 and 1500 ppm.

One end of Zilver stent was positioned on a mandrel. The nozzle was positioned about 100 mm from the stent and the stent was coated with about 419 μg of the mixture, while passing the nozzle over six loops of the stent surface. A power setting of 1.0 watts was used. The weight of mixture coated onto the stent was determined by weighing the stent before and after the coating procedure.

The stent was then over coated with a 4 mg/ml solution of PLA in dichloromethane using the ultrasonic procedure described above. Here, the nozzle was positioned at 4 mm from the stent and deposition performed over eight loops of the stent surface. About 216 μg of PLA was deposited onto the stent surface.

The elution time of the antisense drug was determined using the UV analysis method of Example 1. FIG. 1 shows the elution of the antisense agent from the stent.

Example 3

Coating with Two Barrier Layers

A Zilver stent was coated with about 320 μg of a mixture containing 4 mg/ml Resten-NG antisense drug and 5 mg/ml NBCA using the ultrasonic deposition method described in Example 2. A PLA overcoat (99 μg) was the applied, again using the ultrasonic method. Finally, 220 μg of NBCA was applied using the ultrasonic method.

Figure 2:
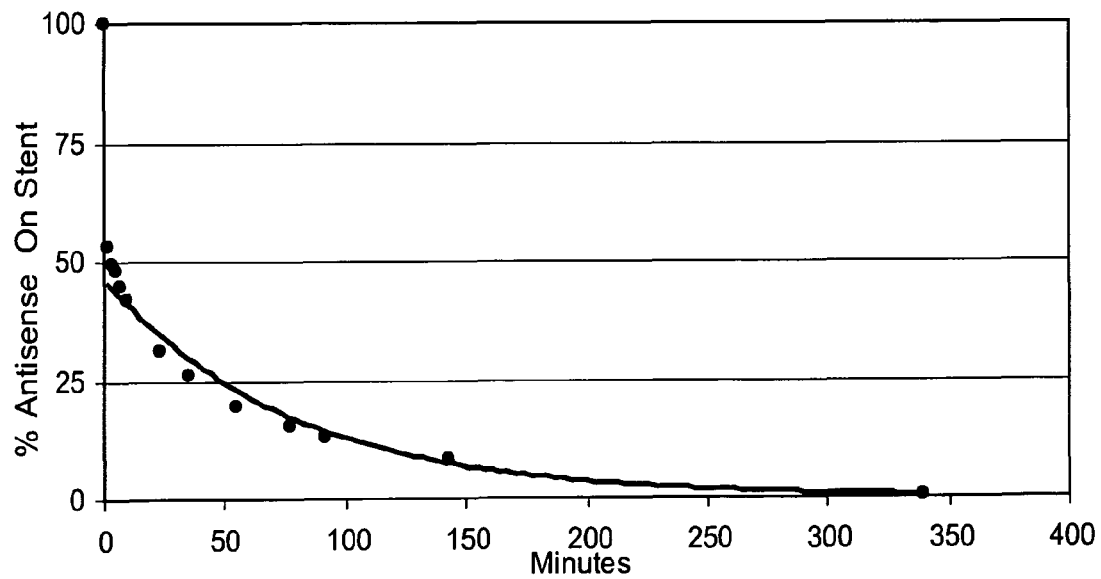
FIG. 2 is a graph showing the elution of the antisense drug from a 8×20 mm stent ultrasonically coated with a mixture of RESTEN-NG™ antisense drug and poly(n-butyl cyanoacrylate), then over coated ultrasonically, first with an over coating of polylactic acid, and then with an over coating of poly (n-butyl cyanoacrylate). The elution followed first order kinetics with a $t_{1/2}$ of 54.1 minutes.

The elution time of the antisense drug was determined using the UV analysis method of Example 1. FIG. 2 shows the elution of the antisense agent from the stent.

Example 4

Coating with Three Barrier Layers

A solution of 50:50 MeOH:CHCl$_3$ containing 4 mg/ml Resten-NG antisense drug was coated onto a Zilver stent using the electrostatic coating method described in Example 1. The nozzle was placed about 40 mm from the stent surface and a total of about 280 μg of antisense drug coated onto the stent.

The stent was then over coated with about 117 μg of PLA using a Badger No. 200 spray gun containing a solution of 4 mg/ml PLA in dichloromethane as described in Example 2. A second overcoat of about 240 μg NBCA was then applied using the electrostatic method. Finally, a third overcoat of 100 μg of PLA was applied using the ultrasonic nozzle.

Figure 3:
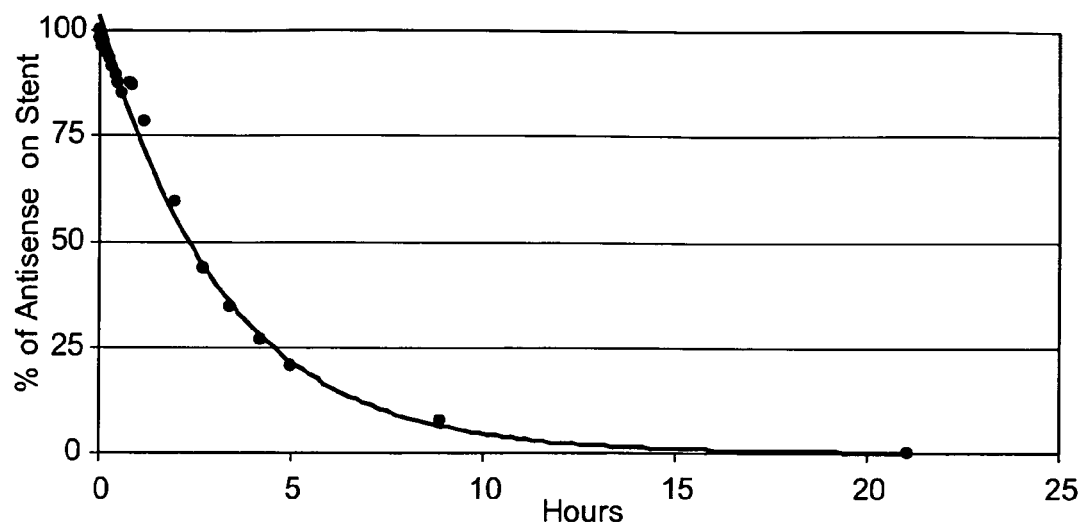
FIG. 3 is a graph showing the elution of the antisense drug from a 10×20 mm stent having an electrostatic coating of RESTEN-NG™ antisense drug, a first over coating of polylactic acid applied with a pressure spray gun, a second coating of poly(n-butyl cyanoacrylate) applied electrostatically and a final ultrasonic over coating of polylactic acid. The elution followed first order kinetics with a $t_{1/2}$ of 2.22 hours.

The elution time of the antisense drug was determined using the UV analysis method of Example 1. FIG. 3 shows the elution of the antisense agent from the stent.

Example 5

Coating with Two Barrier Layers

A Zilver stent was coated with about 340 μg of a mixture containing 4 mg/ml Resten-NG antisense drug and 6 mg/ml NBCA using the electrostatic deposition method described in Example 1. The stent was then over coated with about 200 μg of PLA using the ultrasonic nozzle.

Figure 4:
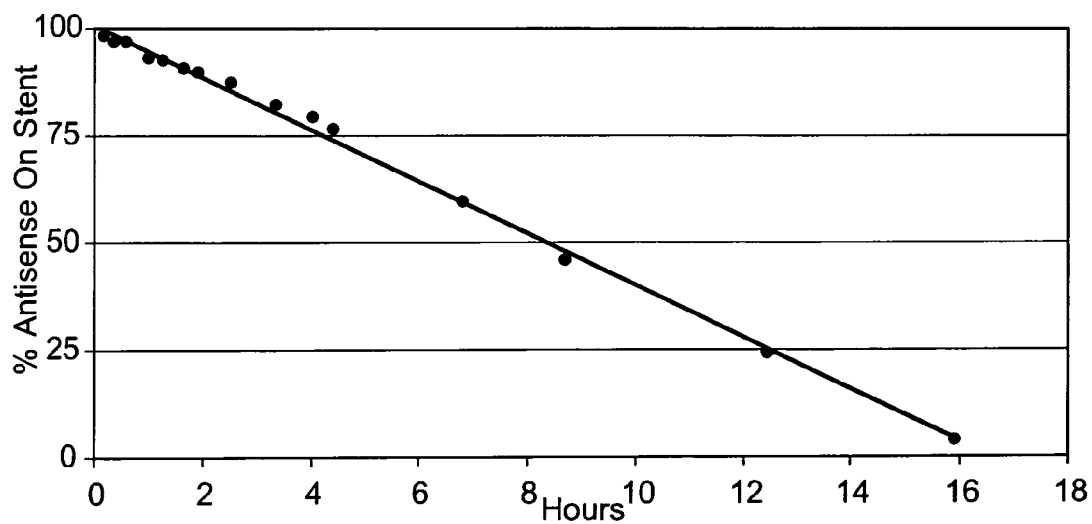
FIG. 4 is a graph showing the elution of the antisense drug from a 8×20 mm stent electrostatically coated with a mixture of RESTEN-NG™ antisense drug and poly(n-butyl cyanoacrylate) and an ultrasonic overcoat of polylactic acid. The elution followed zero order kinetics with a $t_{1/2}$ of 8.36 hours.

The elution time of the antisense drug was determined using the UV analysis method of Example 1. FIG. 4 shows the elution of the antisense agent from the stent.

Example 6

Gamma Sterilization

Figure 5:
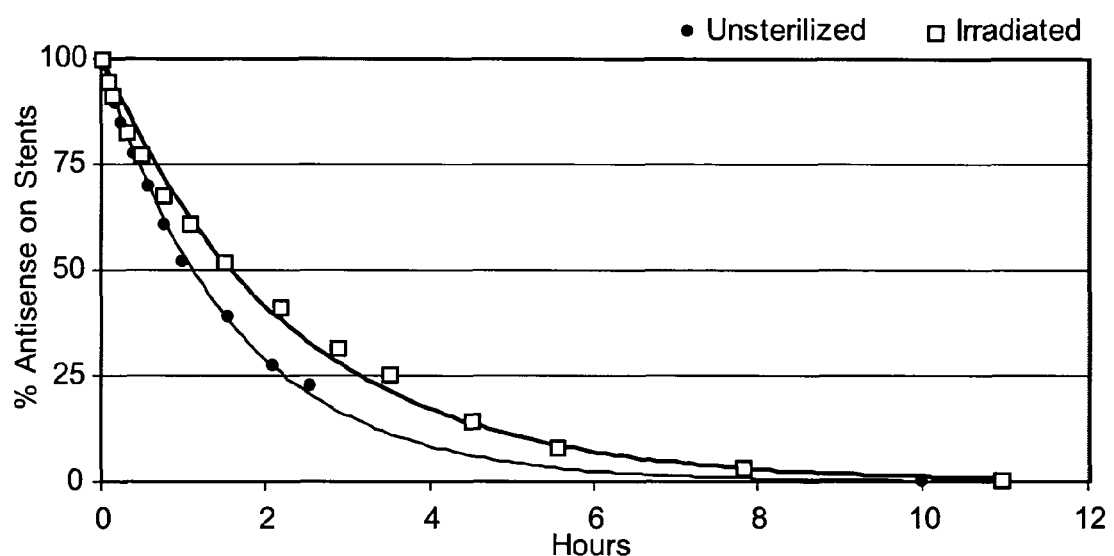
FIG. 5 is a graph showing the elution of the antisense drug from two stents ultrasonically coated with a mixture of RESTEN-NG™ antisense drug and poly(n-butyl cyanoacrylate) and an ultrasonic overcoat of polylactic acid. ●—Stent was crimped to 7 fr, loaded into a COOK stent delivery system, deployed, and eluted in 0.1% PBS. The elution followed first order kinetics with a $t_{1/2}$ of 1.12 hours. ■—Stent was crimped to 7 fr, loaded into a COOK stent delivery system, gamma irradiated at Steris® (Morton Grove, Ill.) at 27 kGy, deployed, and eluted in 0.1% PBS. The elution followed first order kinetics with a $t_{1/2}$ of 1.57 hours.

Two 6×20 mm Zilver stents were ultrasonically coated with about 275 μg and 300 μg of a mixture containing 4 mg/mL Resten-NG antisense drug and 5 mg/mL NBCA using the ultrasonic deposition method described in Example 2. The stents were then ultrasonically over coated with about 292 μg and 325 μg of PLA respectively. One stent was crimped to 7 fr, loaded into a COOK stent delivery system, deployed, and eluted in 0.1% PBS. Its elution followed first order kinetics with a t$_{1/2}$ of 1.12 hours. The other stent was crimped to 7 fr, loaded into a COOK stent delivery system, gamma irradiated at Steris® (Morton Grove, Ill.) at 27 kGy, deployed, and eluted in 0.1% PBS. This elution followed first order kinetics with a $t_{1/2}$ of 1.57 hours. The elution times of the antisense drug were determined using the UV analysis method of Example 1. FIG. 5 shows the elution of the antisense agent from the stents.

What is claimed is:

1. An implantable medical device having at least one surface,
 a first mixture comprising an antisense compound and a poly(alkyl cyanoacrylate) polymer coated directly on the at least one surface to form a first polymer layer, and
 a second mixture comprising a solvent and a biodegradable polymer coated directly on at least a portion of the first layer to form a second polymer layer that is the outermost layer of the device, wherein the second mixture is free of the antisense compound.

2. The implantable medical device of claim 1, wherein the second polymer is polylactic acid and the poly(alkyl cyanoacrylate) polymer is poly(n-butyl cyanoacrylate).

3. The implantable medical device of claim 1, wherein the antisense compound has a solubility in water of greater than 2.5 g/L.

4. The implantable medical device of claim 3, wherein the antisense compound has a solubility in water of greater than 25 g/L.

5. The implantable medical device of claim 1, wherein the poly(alkyl cyanoacrylate) polymer is selected from a group consisting of poly(n-butyl cyanoacrylate), poly(isohexyl cyanoacrylate), poly(n-hexyl cyanoacrylate) and poly(n-octyl cyanoacrylate) and wherein the release of the antisense compound into an environment in which the implantable medical device is placed is controlled by the poly(alkyl cyanoacrylate) polymer.

6. The implantable medical device of claim 1, wherein the antisense compound is selected from a group consisting of an anti-thrombocytic agent, an anti-inflammatory agent and an anti-proliferative agent.

7. The implantable medical device of claim 1, wherein the antisense compound is selected from a group consisting of a natural nucleic acid oligonucleotide and a nucleic acid oligonucleotide having a modified backbone.

8. The implantable medical device of claim 7, wherein the antisense compound is a nucleic acid oligonucleotide having a modified backbone.

9. The implantable medical device of claim 8, wherein the antisense compound inhibits cellular proliferation.

10. The implantable medical device of claim 1, wherein the poly(alkyl cyanoacrylate) polymer comprises an alkyl group comprising between 3 and 12 carbon atoms.

11. The implantable medical device of claim 10, wherein the poly(alkyl cyanoacrylate) polymer is selected from a group consisting of poly(n-butyl cyanoacrylate), poly(isohexyl cyanoacrylate), poly(n-hexyl cyanoacrylate) and poly(n-octyl cyanoacrylate).

12. The implantable medical device of claim 11, wherein the poly(alkyl cyanoacrylate) polymer is poly(n-butyl cyanoacrylate).

13. The implantable medical device of claim 1, wherein the second polymer is selected from a group consisting of polylactic acid, poly-L-lactic acid, poly(D,L-lactide), poly(lactide-co-glycolide), poly(ethylene glycol), polyglycolide and block copolymers of these compounds.

14. The implantable medical device of claim 13, wherein the second polymer is polylactic acid.

15. The implantable medical device of claim 1, wherein the implantable medical device comprises a vascular stent.

16. The implantable medical device of claim 2, wherein the antisense compound is coated on the least one surface of the implantable medical device, wherein the poly(alkyl cyanoacrylate) polymer is coated on at least a portion of the antisense compound and wherein the second polymer is coated on at least a portion of the poly(alkyl cyanoacrylate) polymer.

17. An implantable medical device having at least one surface and having a first layer consisting essentially of an antisense compound and a poly(alkyl cyanoacrylate) polymer coated directly on the at least one surface, and a second polymer coated directly onto at least a portion of the first layer, wherein the second polymer is a biodegradable polymer forming an outermost surface of the device,
 wherein the poly(alkyl cyanoacrylate) polymer comprises an alkyl group comprising between 3 and 12 carbon atoms,
 wherein the second polymer is selected from a group consisting of polylactic acid, poly-L-lactic acid, poly(D,L-lactide), poly(lactide-co-glycolide), poly(ethylene glycol), polyglycolide and block copolymers of these compounds and
 wherein the poly(alkyl cyanoacrylate) polymer and the second polymer are present at a weight ratio of between 400:1 and 1:400.

18. The implantable medical device of claim 1, wherein the second polymer is applied by a spray coating method.

19. The implantable medical device of claim 18, wherein the second polymer is applied by an ultrasonic spray coating method.

20. The implantable device of claim 1, wherein first polymer layer consists of an antisense compound and a poly(alkyl cyanoacrylate) polymer.

* * * * *